(12) United States Patent
Pierce

(10) Patent No.: US 9,439,696 B2
(45) Date of Patent: Sep. 13, 2016

(54) IMPLANT TO STRESS BONE TO ALTER MORPHOLOGY

(75) Inventor: Andrew Lee Pierce, Warsaw, IN (US)

(73) Assignee: BIOMET MANUFACTURING, LLC, Warsaw, IN (US)

( * ) Notice: Subject to any disclaimer, the term of this patent is extended or adjusted under 35 U.S.C. 154(b) by 1127 days.

(21) Appl. No.: 13/162,801

(22) Filed: Jun. 17, 2011

(65) Prior Publication Data

US 2012/0323287 A1 Dec. 20, 2012

(51) Int. Cl.
*A61B 17/80* (2006.01)
*A61B 17/56* (2006.01)
*A61B 17/66* (2006.01)
*A61B 17/64* (2006.01)

(52) U.S. Cl.
CPC ........... *A61B 17/8004* (2013.01); *A61B 17/56* (2013.01); *A61B 17/66* (2013.01); *A61B 17/8014* (2013.01); *A61B 17/6441* (2013.01); *A61B 17/8023* (2013.01); *A61B 2017/565* (2013.01)

(58) Field of Classification Search
CPC ................. A61B 17/8004; A61B 17/8014
USPC ..................... 606/57, 58, 280–299
See application file for complete search history.

(56) References Cited

U.S. PATENT DOCUMENTS

| | | | |
|---|---|---|---|
| 3,528,085 A * | 9/1970 | Reynolds, Jr. | 606/282 |
| 3,552,389 A * | 1/1971 | Allgower et al. | 606/282 |
| 4,219,015 A | 8/1980 | Steinemann | |
| 5,122,140 A * | 6/1992 | Asche et al. | 606/55 |
| 5,304,180 A | 4/1994 | Slocum | |
| 5,437,668 A * | 8/1995 | Aronson et al. | 606/57 |
| 5,728,095 A * | 3/1998 | Taylor et al. | 606/54 |
| 6,488,685 B1 | 12/2002 | Manderson | |
| 7,341,589 B2 | 3/2008 | Weaver et al. | |
| 7,736,365 B2 | 6/2010 | Phillips et al. | |
| 7,811,312 B2 * | 10/2010 | Stevens et al. | 606/280 |
| 8,083,740 B2 * | 12/2011 | Eslami et al. | 606/56 |
| 2005/0234448 A1 * | 10/2005 | McCarthy | 606/57 |
| 2005/0256526 A1 * | 11/2005 | Johnston | 606/69 |
| 2007/0270850 A1 * | 11/2007 | Geissler | 606/69 |
| 2008/0039861 A1 * | 2/2008 | Ahmad et al. | 606/105 |
| 2008/0051779 A1 * | 2/2008 | Mackenzie et al. | 606/57 |
| 2008/0269741 A1 * | 10/2008 | Karidis | 606/56 |
| 2008/0311542 A1 * | 12/2008 | Rana et al. | 433/140 |
| 2009/0131987 A1 | 5/2009 | Matityahu | |
| 2009/0143825 A1 | 6/2009 | Graham et al. | |
| 2009/0326591 A1 | 12/2009 | Spencer, Jr. | |

(Continued)

*Primary Examiner* — Andrew Yang
(74) *Attorney, Agent, or Firm* — Schwegman Lundberg & Woessner, P.A.

(57) ABSTRACT

An implant operable to alter morphology of a long bone can comprise a first longitudinal member, a second longitudinal member, and an adjusting member. The first longitudinal member can have a bone attachment end and a first connecting end. The second longitudinal member can have a second bone attachment end and a second connecting end. The adjusting member can connect to both of the first and second connecting ends. The adjusting member can be selectively moveable from a first implanted position where the first and second connecting ends are fixed to respective ends of the long bone and spaced apart a first distance to a second implanted position where the first and second connecting ends are fixed to the respective ends of the long bone and spaced apart a second distance. The second distance is less than the first distance causing a long bone to be compressed between the first and second bone attachment ends.

11 Claims, 3 Drawing Sheets

(56) References Cited

U.S. PATENT DOCUMENTS

| | | | |
|---|---|---|---|
| 2010/0131013 A1 | 5/2010 | Ralph et al. | |
| 2010/0312243 A1* | 12/2010 | Ross et al. | 606/56 |
| 2011/0230885 A1* | 9/2011 | Weiner et al. | 606/71 |
| 2011/0245830 A1* | 10/2011 | Zgonis et al. | 606/57 |
| 2012/0316561 A1* | 12/2012 | Dubois | 606/58 |

* cited by examiner

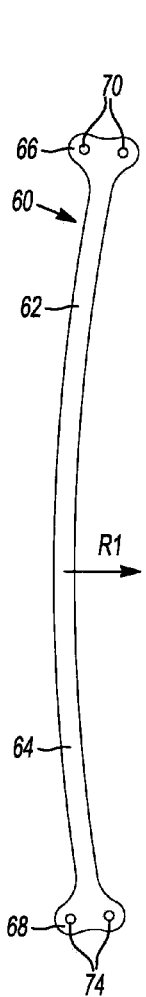
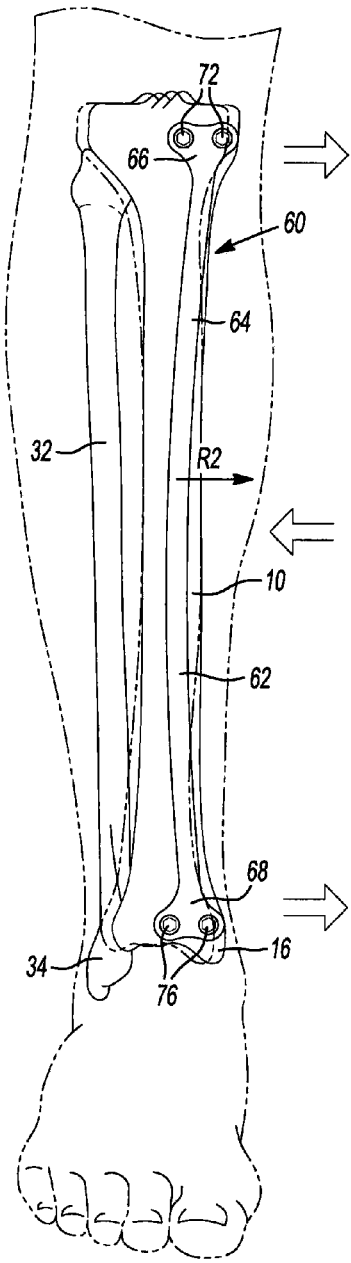
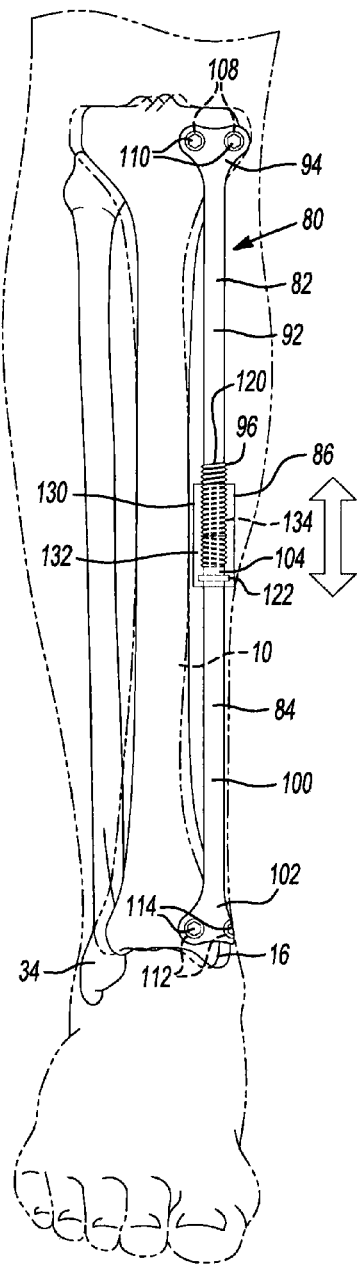
Fig-3
Fig-4
Fig-5

IMPLANT TO STRESS BONE TO ALTER MORPHOLOGY

FIELD

The present disclosure relates generally to long bones and more particularly to various implants and methods for reshaping a long bone that may have an unsatisfactory mechanical axis.

BACKGROUND

This section provides background information related to the present disclosure which is not necessarily prior art.

In some examples, a long bone such as a tibia may become misaligned relative to a knee causing cartilage degeneration and/or joint misalignment. In these examples, it may be desired to reshape the bone in an effort to shift the mechanical axis of the bone such as to unload a diseased knee compartment. One known method of correcting various misalignments is an osteotomy that includes cutting the bone and allowing the bone to regrow in the area of the cut. In some examples, a surgeon may cut out a wedge or similar shape to facilitate the realignment and resultant bone growth. In some examples however, cutting the bone in this manner may be unsatisfactory.

SUMMARY

This section provides a general summary of the disclosure, and is not a comprehensive disclosure of its full scope or all of its features.

An implant operable to alter morphology of a long bone can comprise a first longitudinal member, a second longitudinal member, and an adjusting member. The first longitudinal member can have a bone attachment end and a first connecting end. The second longitudinal member can have a second bone attachment end and a second connecting end. The adjusting member can connect to both of the first and second connecting ends. The adjusting member can be selectively moveable from a first implanted position to a second implanted position. In the first implanted position, the first connecting end and the second connecting end are fixed to respective ends of the long bone and spaced apart a first distance. In the second implanted position, the first connecting end and the second connecting end are fixed to the respective ends of the long bone and spaced apart a second distance. The second distance is less than the first distance causing a long bone to be compressed between the first and second bone attachment ends.

According to additional features, the first bone attachment end can define at least one passage. The second bone attachment end can define at least one passage. The implant can further comprise bone screws that are configured to be received by the respective passages. One of the first and second connecting ends can comprise a first threaded portion. One of the adjusting member or the other of the first and second connecting ends can comprise a second threaded portion. The first and second threaded portions can be configured to threadably mate. The first connecting end can comprise the first threaded portion. The adjusting member can comprise the second threaded portion. The first threaded portion can comprise a male threaded portion and the adjusting member can comprise a female threaded portion.

According to other features, the second connecting end can comprise a raised collar that engages a complementary raised flange formed on the adjusting member. The adjusting member can comprise a cylindrical sleeve that has a complementary raised flange. The cylindrical sleeve also comprises the female threaded portion. The complementary raised flange and the threaded portion are both formed on an inner diameter of the cylindrical sleeve.

A method of altering morphology of a long bone according to the present teachings can comprise coupling a first bone attachment end of a longitudinal plate to a first portion of the long bone. The long bone can be distracted without fracturing the long bone. A second bone attachment end of the longitudinal plate can be coupled to a second portion of the long bone causing the long bone to be in compression at a first area of the long bone and be in tension at a second area of the long bone.

According to additional features of the instant method, distracting the long bone can comprise applying a force onto the second portion of the long bone such that a distance between the first and second portions of long bone changes. Distracting the long bone can comprise applying a force onto the second portion of the long bone such that a distance between the first and second portions is reduced.

According to other features of the instant method, coupling the first and second bone attachment ends can comprise advancing bone screws through passages defined through the first and second attachment ends of the longitudinal plate and into the long bone. According to one example, prior to the distracting, the long bone has a first mechanical axis. Subsequent to coupling the second long bone attachment end, the long bone has a second mechanical axis. The first and second mechanical axes are different.

A method of altering morphology of a long bone according to another example of the present teachings can include coupling a first bone attachment end of a longitudinal plate to a first portion of the long bone. A securing member can be advanced through an opening in the longitudinal plate and partially into the long bone. The securing member is continued to be advanced into the long bone such that a portion of the securing member slidably engages the longitudinal plate causing the longitudinal plate to be in tension between the first bone attachment end and the opening while concurrently causing a portion of the long bone to be in compression.

According to other features of the instant method, coupling the first bone attachment end of the longitudinal plate can comprise advancing at least one bone screw through a passage defined through the first bone attachment end. Advancing the securing member can comprise advancing a screw having a threaded distal end and a conical proximal head. The continuing of the advancing of the securing member can comprise slidably advancing the conical proximal head along the longitudinal plate at the opening. Advancing the conical proximal head can comprise slidably advancing the conical head along a ramp portion defined on the longitudinal plate at the opening.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a plan view of an implant constructed in accordance to a second example of the present teachings and prior to implantation.

FIG. 4 is an anterior view of an exemplary tibia and shown subsequent to implantation of the implant of FIG. 3.

FIG. 5 is an anterior view of an exemplary tibia shown with an implant constructed in accordance to a third example of the present teachings and shown prior to adjusting an adjusting member of the implant and subsequent to adjusting the adjusting member of the implant.

Corresponding reference numerals indicate corresponding parts throughout the several views of the drawings.

DETAILED DESCRIPTION

Figure 1:
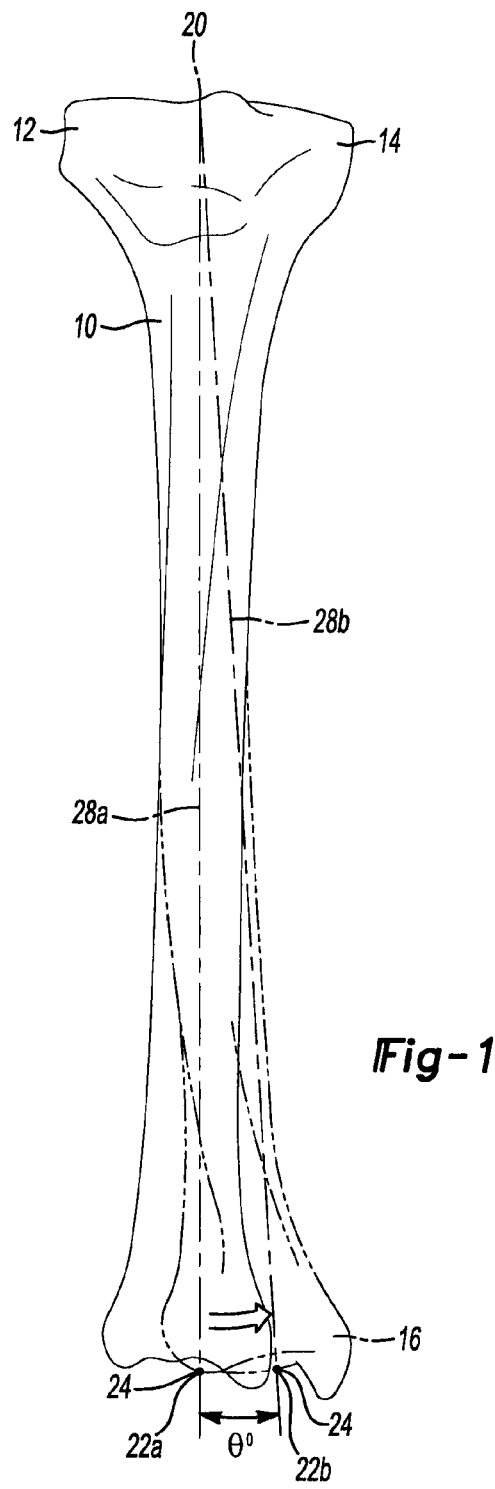
FIG. 1 is an anterior view of an exemplary tibia shown prior to altering its axis (solid line) and subsequent to altering its axis according to the present teachings (phantom line).

Example embodiments will now be described more fully with reference to the accompanying drawings.

The following description will be directed toward an implant and method for altering morphology of a long bone. The exemplary description will be directed toward a right tibia 10. The tibia 10 generally includes a lateral condyle 12, medial condyle 14, and medial malleolus 16. An axis of the tibia 10 is generally defined between a point 20 taken through a horizontal slice of the proximal tibia and a point 22a extending through the talus 24. As viewed in FIG. 1, the axis 28 is therefore identified between the points 20 and 22a. The axis 28 will be referred to herein as an initial axis. The implants and methods according to the present teachings are directed toward realigning this initial axis 28a to a desired axis 28b. The desired axis 28b can therefore be defined between the point 20 and a point 22b. The initial axis 28a and the desired axis 28b can therefore provide an angle Θ therebetween. It will be appreciated that according to the present teachings, various implants and methods will be described herein where the tibia 10 will be described as being "bent". The intent however, is not necessarily to reshape the intermediate portion of the tibia 10 to have a bent or bowed contour. The intent is to ultimately change the long axis of the bone and therefore change the angle Θ.

Figure 2:
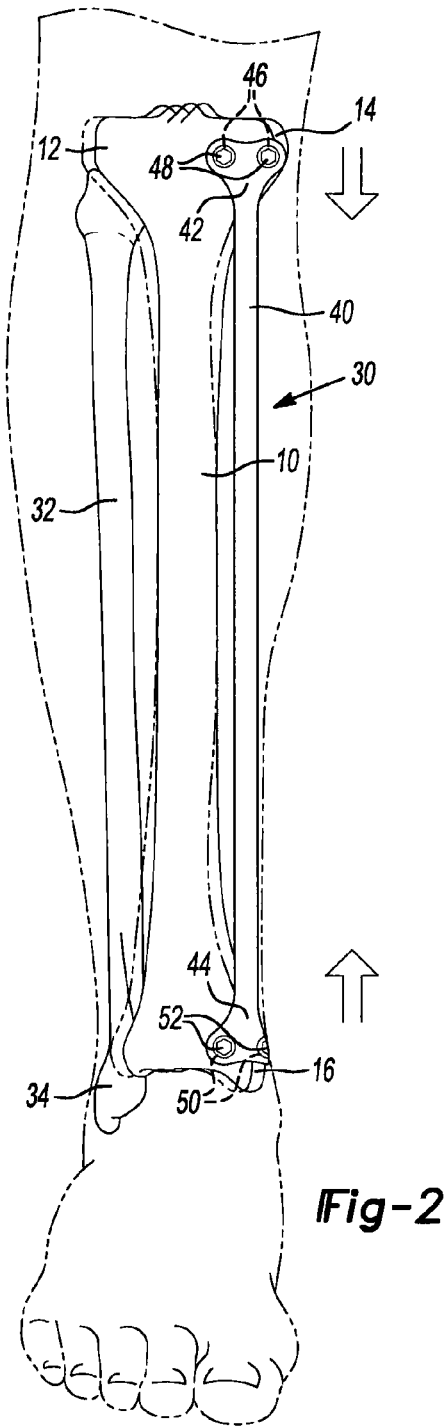
FIG. 2 is an anterior view of an exemplary right tibia and fibula of an exemplary patient and shown with an implant implanted according to one example of the present teachings.

Turning now to FIG. 2, an exemplary implant 30 will be described. The tibia 10 is shown together with a fibula 32 having a lateral malleolus 34. In the example shown in FIG. 2, the tibia 10 is shown generally before manipulation with the implant 30 in phantom line and after manipulation in solid line. The implant 30 generally comprises a longitudinal member 40 having a first bone attachment end 42 and a second bone attachment end 44. The longitudinal member 40 can be generally in the form of a plate or rod or other elongated structure. The first bone attachment end 42 defines passages 46 for receiving bone screws 48 therein. Similarly, the second bone attachment end 44 defines passages 50 for receiving bone screws 52 therethrough.

In one example of implanting the implant 30, a surgeon can first bend or deflect the tibia 10 toward a profile suitable to attain the desired axis. In this regard, a surgeon can apply stress to the tibia 10 and fix the tibia 10 while in a stressed or deflected position. In one example, one of the first or second bone attachment ends 42 or 44 can be secured to the proximal or distal tibia with the bone screws 48 or 52. With one end of the implant 30 secured to the tibia, a surgeon can apply a force at an opposite end of the tibia while concurrently securing the other of the first or second bone attachment end 42 or 44 to the tibia. As can be appreciated, the implant 30 will tend to draw the proximal and distal ends of the tibia toward each other and encourage the tibia 10 to reshape to accommodate this stress as a result of the tibia's natural remodeling mechanism. It will be appreciated that a series of implants 30 having different lengths can be provided to a surgeon to accommodate tibias of different lengths. It will also be appreciated that in some examples, a surgeon can use a first implant 30 to reshape the tibia to a first position and once the first position is attained, a surgeon can implant another implant 30, or manipulate the first implant 30 to further encourage the bone to reshape. In other words, the reshaping of the tibia 10 may be conducted with multiple steps.

Turning now to FIG. 3, an implant 60 is shown. The implant 60 generally comprises a longitudinal member 62 having a main body 64, a first bone attachment end 66, and a second bone attachment end 68. The first bone attachment end 66 can define passages 70 for receiving bone screws 72. Similarly, the second bone attachment end 68 can define passages 74 configured to receive bone screws 76. The main body 64 of the implant 60 can generally have an arcuate profile that defines a radius R1.

Turning now to FIG. 4, the tibia 10 is shown prior to implantation of the implant 30 in phantom line and subsequent to implantation of the implant 30 in solid line. Again, in some examples, a surgeon can first secure either the first or second bone attachment end 66 or 68 to the tibia 10. Next, a surgeon can apply a force to the opposite end of the tibia 10 while securing the other of the first or second bone attachment ends 66 or 68 to the tibia. As shown in FIG. 4, the main body 64 of the implant 60 now defines a radius R2. In the implanted position, the radius R2 is greater than the radius R1. As can be appreciated, the main body 64 of the implant 60 will tend to want to return to its original radius R1. In doing so, the first bone attachment end 66 and the second bone attachment end 68 will tend to urge the respective proximal and distal ends of the tibia rightward as viewed in FIG. 4 (medially). Concurrently, an intermediate portion of the main body 64 will tend to therefore influence a corresponding intermediate portion of the tibia 10 leftward as viewed in FIG. 4 (laterally). Again, it will be appreciated that the implant 60 will encourage the tibia 10 to reshape in an effort to realign the axis toward the desired axis 28b (FIG. 1).

Turning now to FIG. 5, an implant constructed in accordance to another example of the present teachings is shown and generally identified at reference numeral 80. The implant 80 generally includes a first longitudinal member 82, a second longitudinal member 84, and an adjusting member 86. The first longitudinal member 82 generally includes an elongated body portion 92 having a first bone attachment end 94 and a first connecting end 96. The second longitudinal member 84 can generally comprise a longitudinal body portion 100 having a second bone attachment end 102 and a second connecting end 104. The first bone attachment end 94 can generally define passages 108 configured to receive bone screws 110 therein. Similarly, the second bone attachment end 102 can define passages 112 configured to receive bone screws 114 therein. While the first and second longitudinal members 82 and 84 are shown as having a generally linear profile, one or both of them can define an arcuate profile. The first connecting end 96 can generally include a threaded portion 120. The second connecting end 104 can define an annular flange 122 thereon. Those skilled in the art will appreciate that the threaded portion 120 can alternatively be provided on the second connecting end 104 while the raised flange 122 can be provided on the first connecting end 96. The adjusting member 86 can generally comprise a cannulated cylindrical body 130 having a raised collar 132 and female threads 134 formed thereon.

An exemplary method of implanting and using the implant 80 will now be described. Again, the tibia 10 is shown prior to implantation of the implant 80 in phantom line and subsequent to implantation of the implant 80 in solid line. At the outset, a surgeon can attach one of the first or second bone attachment ends 94 or 102 to the tibia. Next, a surgeon may apply a force to the opposite end of the tibia while connecting the other of the first or second bone attachment ends 94 and 102 to the tibia. In another example, a surgeon can attach both of the first and second bone attachment ends 94 and 102 to the tibia 10 without applying an external force onto the tibia 10.

The adjusting member 86 can then be rotated such that the female threads 134 of the cylindrical body 130 threadably advance along the threads 120 on the first connecting end 96. As can be appreciated, the raised flange 122 on the adjusting member 86 will engage and pull the raised collar 132 (upward as viewed in FIG. 5) on the second longitudinal member 84. Continued advancement of the adjusting member 86 will tend to urge the respective proximal and distal ends of the tibia toward each other thereby reshaping the tibia 10 and altering the desired axis (28b, FIG. 1). According to some examples, it may be desirable for a surgeon to advance the adjusting member 86 a first distance along the threads 120 on the first connecting end 96 and allow the tibia to reshape to accommodate such an initial force. Thereafter, a surgeon can then advance the adjusting member 86 further along the first connecting end 96 to encourage the tibia 10 to further reshape. As can be appreciated, one or many adjustment periods may be desired depending on a particular patient.

Figure 8:
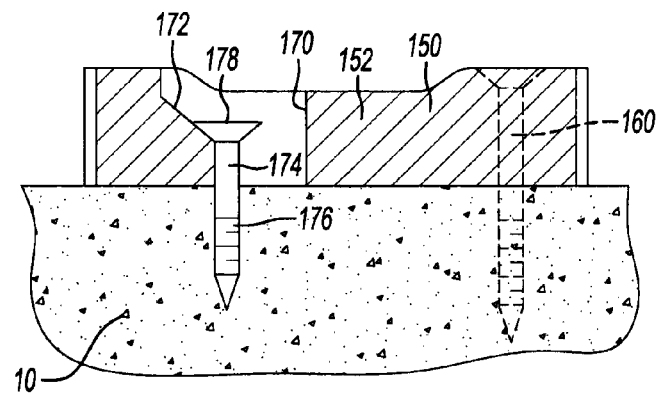
FIG. 8 is a cross-sectional view of the implant of FIG. 7 taken along lines 8-8 and shown with a securing member initially driven into the bone.
Figure 9:
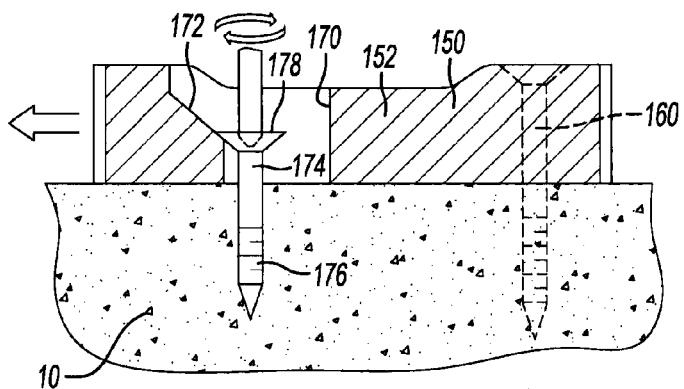
FIG. 9 is a cross-sectional view of the implant of FIG. 8 and shown with the securing member further advanced into the bone causing a conical head of the securing member to urge a portion of the implant leftward causing the implant to be in tension while concurrently placing the adjacent bone in compression.

Turning now to FIGS. 6-9, an implant 150 constructed in accordance to additional features of the present teachings will be described. The implant 150 generally includes a longitudinal body 152 having a first end 154 and a second end 156. In one example, the longitudinal body 152 can include a longitudinal plate. The first end 154 generally defines passages 158 configured to receive bone screws 160 therein. The second end 156 can optionally define passages 164 therethrough. The implant 150 can define an opening 170 therethrough. The opening 170 can further be defined by a ramp 172 (FIGS. 8-9). In one example, the opening 170 can define a generally oblong profile. The opening 170 can be configured to receive a securing member 174 therein. The securing member 174 can generally include a distal threaded end 176 and a conical head 178.

Figure 6:
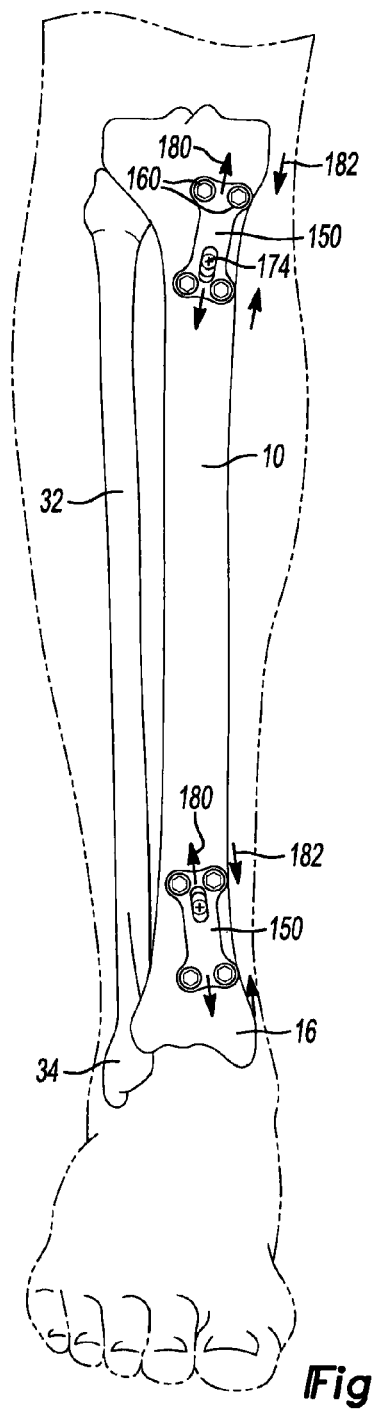
FIG. 6 is an anterior view of an exemplary tibia shown with a pair of implants constructed in accordance to a fourth example of the present teachings and illustrating the implants being placed in tension causing the adjacent bone to therefore be in compression.
Figure 7:
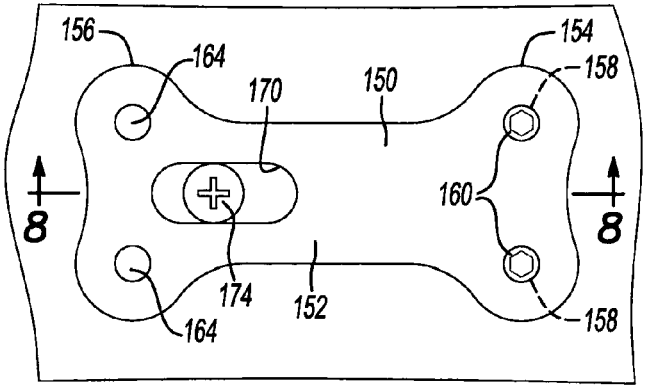
FIG. 7 is a plan view of an implant shown in FIG. 6.

An exemplary method of implanting the implant 150 according to the present teachings will now be described. At the outset, a surgeon can secure the first end 154 of the implant 150 to the tibia 10 by advancing the bone screws 160 through the passages 158. Next, a surgeon can initially locate the securing member 174 into the opening 170 (FIG. 8). The surgeon can then partially advance the distal threaded end 176 into the tibia 10 to a point at which the conical head 178 initially engages the ramp 172 on the body 152 of the implant 150. Next, the surgeon can further advance the securing member 174 into the bone 10 causing the conical head 178 to slidably advance along the ramp 172 and as a result, urge the implant 150 generally away from the bone screws 160. In this regard, and as illustrated in FIG. 9, advancement of the conical head 178 along the ramp 172 urges the implant 150 leftward. As shown in FIG. 6, such an action will cause the implant 150 to generally be in tension illustrated by arrows 180. As a result, the adjacent tibial bone will be placed in compression identified by the arrows 182. It will be appreciated that while there are only two implants 150 shown in FIG. 6, one or a plurality of implants 150 may be strategically located onto the implant 10 for influencing compression as a desired area. Furthermore, it will be appreciated that while the implant 150 is illustrated as having a particular span, the implant 150 may be suitable for influencing a generally localized compression 182 onto the tibia 10. In other examples, the implant 150 may be much longer so as to span a greater length of the tibia such that a compressive force 182 can be influenced generally along a greater distance of the tibia 10.

In each of the examples discussed herein, the implants 30, 60, 80, and 150 can be removed from the tibia 10 once desirable reshaping of the tibia 10 has occurred. The tibia 10 will tend to remain in the newly reshaped orientation subsequent to removal of the implants 30, 60, 80, and 150. It will also be appreciated that the reshaping may be accomplished sequentially with more than one implant being used such as in succession.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of altering morphology of an unbroken long bone, the method comprising:

coupling a first bone attachment end of a longitudinal plate to a first portion of the unbroken long bone;

advancing a securing member through an opening in the longitudinal plate and partially into the unbroken long bone; and continuing the advancing of the securing member into the unbroken long bone such that a portion of the securing member slidably engages the longitudinal plate causing the longitudinal plate to the in tension between the first bone attachment end and the opening while concurrently causing a portion of the unbroken long bone to be in compression to change an angle of a longitudinal axis of the unbroken long bone.

2. The method of claim 1 wherein coupling the first bone attachment end of the longitudinal plate comprises advancing at least one bone screw through a passage defined through the first bone attachment end.

3. The method of claim 1 wherein advancing the securing member comprises advancing a screw having a threaded distal end and a conical proximal head.

4. The method of claim 3 wherein the continuing of the advancing the securing member comprises slidably advancing the conical proximal head along the longitudinal plate at the opening.

5. The method of claim 4 wherein advancing the conical proximal head comprises slidably advancing the conical head along a ramp portion defined on the longitudinal plate at the opening.

6. The method of claim 1, further comprising distracting the long bone without fracturing the long bone by continuing the advancing of the securing member into the long bone.

7. A method of altering morphology of an unbroken long bone, the method comprising:
coupling a first end of a longitudinal plate to a first bone portion of the unbroken long bone;
advancing a securing member through an opening of the longitudinal plate and partially into the unbroken long bone; and
continuing to advance the securing member into the unbroken long bone such that a portion of the securing member slidably engages a ramped portion of the longitudinal plate by sliding down the ramped portion to the unbroken long bone to cause the longitudinal plate to be in tension between the first end and the opening while concurrently causing a portion of the unbroken long bone to be in compression, in order to distract the unbroken long bone to change an angle of a longitudinal axis of the unbroken long bone.

8. The method of claim 7, further comprising arranging the securing member such that a first longitudinal axis of the securing member extends generally perpendicular to a second longitudinal axis extending along a length of the longitudinal plate.

9. The method of claim 7, wherein coupling the first end of the longitudinal plate to the first bone portion includes advancing at least one bone screw through a passage defined through the first bone attachment end.

10. The method of claim 7, wherein advancing the securing member includes advancing a screw having a threaded distal end and a conical proximal head.

11. The method of claim 10, wherein continuing to advance the securing member includes slidably advancing the conical proximal head along the ramped portion.

* * * * *

UNITED STATES PATENT AND TRADEMARK OFFICE
CERTIFICATE OF CORRECTION

PATENT NO. : 9,439,696 B2
APPLICATION NO. : 13/162801
DATED : September 13, 2016
INVENTOR(S) : Andrew Lee Pierce It is certified that error appears in the above-identified patent and that said Letters Patent is hereby corrected as shown below:

In the Claims

In Column 6, Line 63, in Claim 1, delete "the" and insert --be--, therefor

Signed and Sealed this
Sixth Day of March, 2018

Andrei Iancu
*Director of the United States Patent and Trademark Office*